(12) United States Patent
Takaya et al.

(10) Patent No.: US 7,823,469 B2
(45) Date of Patent: Nov. 2, 2010

(54) SAMPLE DISPENSING APPARATUS

(75) Inventors: Eiji Takaya, Mito (JP); Masahito Kakuno, Naka (JP); Satoshi Hagiya, Tokai (JP); Junichi Oizumi, Kasumigaura (JP); Nobuo Suzuki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 486 days.

(21) Appl. No.: 11/964,951

(22) Filed: Dec. 27, 2007

(65) Prior Publication Data

US 2008/0156118 A1    Jul. 3, 2008

(30) Foreign Application Priority Data

Dec. 28, 2006   (JP) .............................. 2006-354675

(51) Int. Cl.
*G01L 3/021* (2006.01)
(52) U.S. Cl. .................................. 73/864.14
(58) Field of Classification Search ........................ None
See application file for complete search history.

(56) References Cited

U.S. PATENT DOCUMENTS 5,178,834 A    1/1993   Kagayama et al.
5,627,522 A    5/1997   Walker et al.

FOREIGN PATENT DOCUMENTS

| AU | 2004200814 | 3/2004 |
|---|---|---|
| EP | 733 905 | 11/1999 |
| JP | 11-304814 | 11/1999 |
| WO | WO01/88549 | 11/2001 |

*Primary Examiner*—Robert R Raevis
(74) *Attorney, Agent, or Firm*—Mattingly & Malur, P.C.

(57) ABSTRACT

A sample dispensing apparatus dispenses a sample from a container accommodating a sample such as blood or urea sampled for checking. This sample dispensing apparatus can prevent internal contamination of the apparatus due to dripping of the sample and abnormal sucking operations caused by drainage, condensation and fixing of the sample. The sample dispensing apparatus according to the present invention comprises a dispensing device for dispensing a sucked sample, a dispensing head provided in the dispensing device, and a disposable nozzle chip dismountably set on the dispensing head. In this apparatus, dispensing of a sample to child sample containers is performed exchanging the child sample containers with new ones. When the state, in which dispensing to the child container cannot be carried out, is continued for a prespecified period of time, the nozzle chip is automatically released from the dispensing head.

7 Claims, 3 Drawing Sheets

SAMPLE DISPENSING APPARATUS

BACKGROUND OF THE INVENTION

1. Field of the Invention

The present invention relates to a sample dispensing apparatus, and more specifically to a sample dispensing apparatus for dispensing a sample with a disposable nozzle chip, carrying out the dispensed samples to a transfer line and transferring the samples.

2. Description of the Related Art

The sample dispensing apparatus is disclosed, for example, in JP-A-11-304814.

The sample dispensing apparatus is operated as follows: A sample is sucked into a disposable nozzle chip with the use of the nozzle chip for each sample and then discharged a small amount of the sample to the another container to automatically distribute a sample such as blood and urine from a container filled with the sample to another container by the amount required for analysis or examination.

A child sample container into which the sample is dispensed is automatically exchanged with a new one. However, when a jam occurs in the downstream from the dispensing device and a new child sample container cannot be carried in to be replaced with a current one, exchange of the child sample container cannot be performed, and the dispensing operation is temporally stopped.

SUMMARY OF THE INVENTION

When a sample is dispensed, the sample is sucked by a disposable nozzle chip from a parent sample container and is dispensed by a prespecified quantity to a plurality of child sample containers. When a number of child sample containers is provided, it is necessary to exchange child sample containers during a series of operations performed when a sample is sucked and discharged.

Exchange of a child sample container to which a sample is discharged with another one is automatically performed. However, when a jam occurs in the downstream from a dispensing device and a new child sample container to be exchanged with a current one cannot be carried in from a dispensing apparatus, the current one cannot be exchanged with a new one, and the dispensing operation is temporally stopped.

In the state where the dispensing operation is stopped and exchange of a child sample container with a new one cannot be performed, a sample remaining in a nozzle chip drips from the nozzle chip and contaminates the inside of the dispensing apparatus.

When the sample in the nozzle chip is dried, condensed, and solidified, the solidified sample will cause clogging when the operation of sucking the sample is restarted.

In view of the problems described above, an object of the present invention is to prevent internal contamination of a dispensing apparatus caused by a sample dripped from a nozzle chip and an abnormal sucking operation caused by a dried and condensed sample within the nozzle chip.

The present invention provides a sample dispensing apparatus comprising: a dispensing device for dispensing a sample sucked therein; a dispensing head provided in the dispensing device; and a disposable nozzle chip detachably mounted on the dispensing head; wherein a sample sucked into the nozzle chip is dispensed into child sample containers while the child sample containers are replaced one by one; and wherein the nozzle chip is released from the dispensing head when a dispensing-suspended time elapses a prespecified period of time, the dispensing-suspended time being a period of time when a dispensing operation of the sample into the child sample container cannot be performed.

More specifically, in the present invention, when a child sample container is exchanged with another one, the dispensing-suspended time when a dispensing head stops with a nozzle chip mounted thereon is measured, and when the dispensing-suspended time elapses a prespecified period of time, the nozzle chip is automatically discarded from the dispensing head, and when the child sample container is exchanged with another one, a new nozzle chip is set on the dispensing head to restart the dispensing operation. With the configuration as described above, the problems as described above can be solved.

With the present invention, a dispensing-suspended time during which restart of exchange of child sample containers is waited is measured, and when a prespecified period of time elapses, a nozzle chip set on a current dispensing head is discarded, so that such troubles as dripping of a sample remaining in a nozzle chip, drying and condensing of the sample, and clogging can be prevented. Thus, it is possible to prevent negative effects by the troubles as described above over a result of analysis by an analyzer or internal contamination of a dispensing apparatus.

DETAIELD DESCRIPTION OF THE PREFERRED EMBODIMENTS

An embodiment of the present invention is described below with reference to FIG. 1 to FIG. 3.

Figure 1:
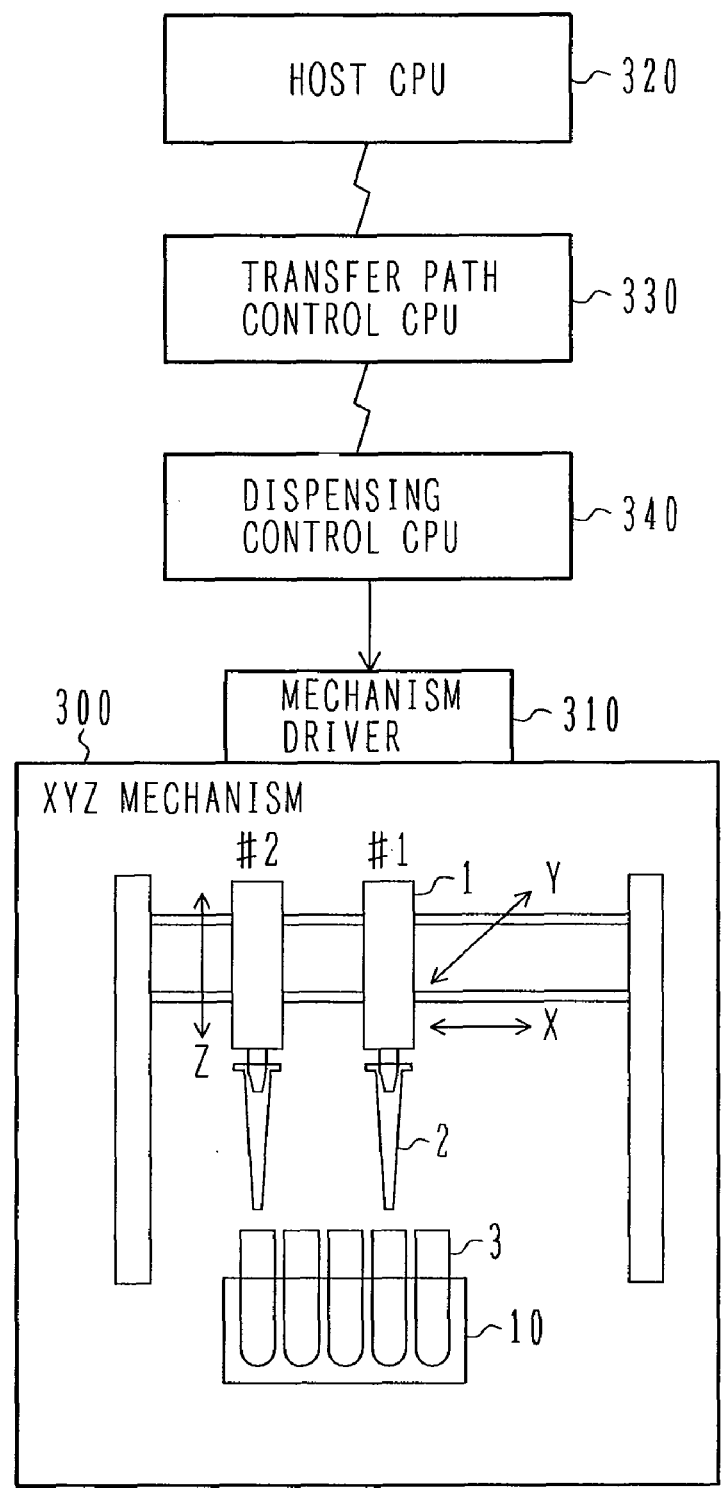
FIG. 1 is a view illustrating a configuration of a control system according to an embodiment of the present invention.

FIG. 1 is a view illustrating an example of a configuration of a control system according to the present invention.

A plurality of dispensing heads 1 (#1 and #2 in FIG. 1) are mounted on an XYZ movement mechanism 300 and are used for dispensing a sample such as blood serum or urea.

A dispensing device includes the XYZ mechanism 300 holding the dispensing head 1 and moving in the vertical direction as well as in the horizontal direction, and a mechanism driver 310 for driving the XYZ mechanism.

The dispensing head 1 mainly comprises a nozzle base on which a nozzle chip 2 is mounted, a vacuum sucking section for sucking and discharging a sample, a pressure detector for converting a pressure change in sucking or discharging to an electric signal, and a signal processing circuit, and sucks and discharges a sample from a hole provided at a tip of the nozzle chip 2.

Although the signal processing circuit is not shown in the figure, the circuit processes signals output from the pressure sensor mounted in the dispensing head 1 and executes operations such as dispensing, detecting and shooting troubles.

A host CPU (Central Processing Unit) 320, a transfer path control CPU 330, and a dispense control CPU 340 are connected to each other through a local data communication line. The transfer path control CPU controls transfer of sample racks.

The dispense control CPU 340 executes control on inquiry of dispense instruction information to the host CPU 320 according to a rack ID (Identity, identification code), transmits information concerning a result of dispensing, and controls the XYZ mechanism 300 included in the dispensing head 1 and a sample transfer mechanism in the dispensing device so that a series of operations for dispensing a sample may be executed.

One or a plurality of parent sample containers 3 each with a parent sample accommodated therein are mounted on a rack 10 for transferring sample containers and are transferred by a rack.

Figure 2:
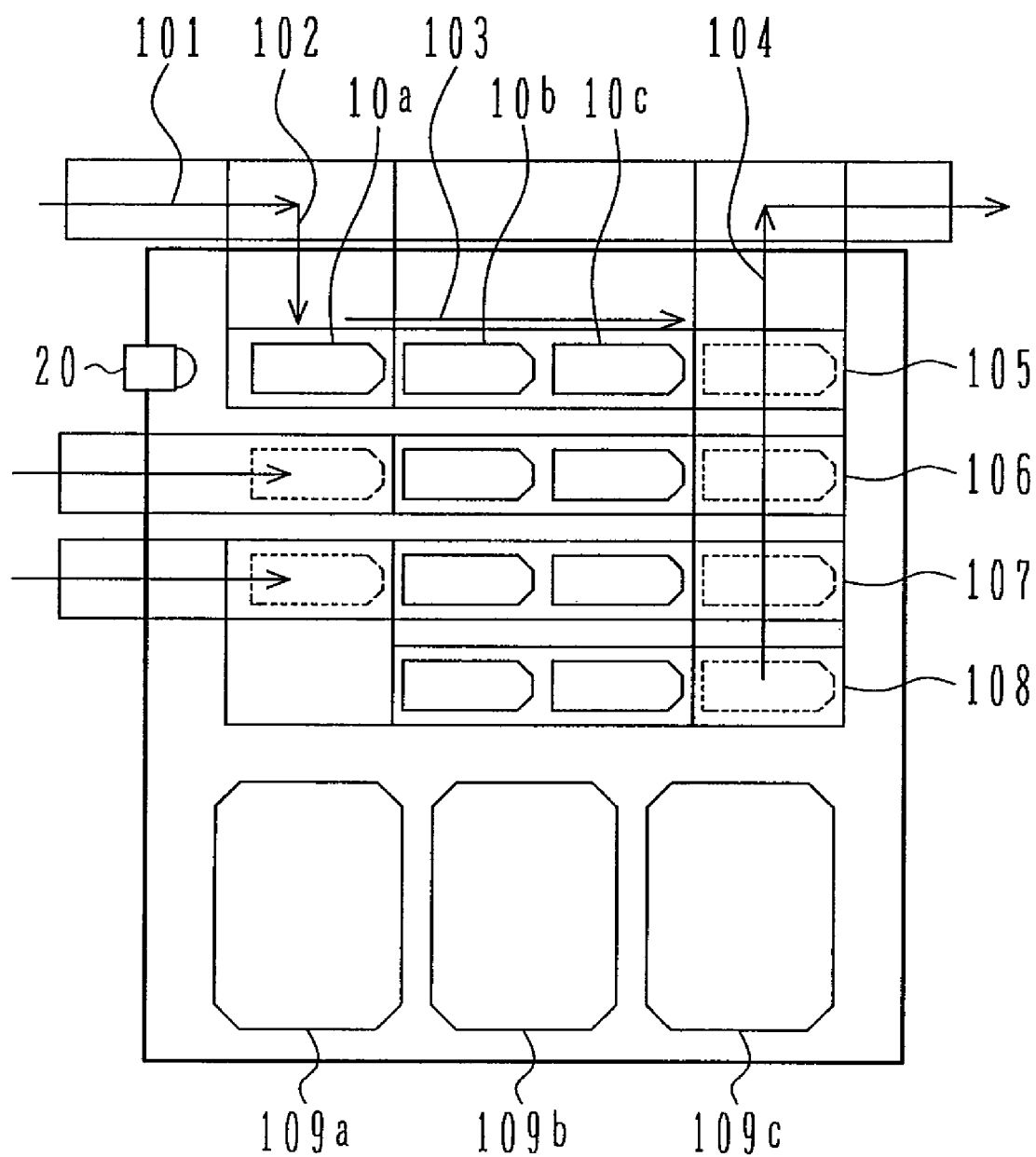
FIG. 2 is a view showing a work area illustrating outline of sample rack carrying operations to be performed by a sample dispensing apparatus according to the embodiment of the present invention.

FIG. 2 is a view showing a work area illustrating outline of sample rack carrying operations to be performed by a sample dispensing apparatus according to the embodiment of the present invention.

The parent sample racks 10a, 10b, and 10c with the parent sample containers transferred through an external transfer line 101 mounted thereon are carried in by a carry-in mechanism 102 into the dispensing device and are transferred on a parent line 103 up to a dispensing position.

In this step, bar code adhered to each rack is read with a bar code reader 20, and the rack is identified according to the rack ID. The racks with child sample containers into which the sample is dispensed are transferred to transfer lines 105, 106, 107, and 108 by a rack supply mechanism not shown, and are transferred to respective dispensing positions.

The dispensing head 1 receives the nozzle chip 2 from chip racks 109a, 109b, and 109c each the nozzle chip 2 mounted thereon to execute operations for sucking and dispensing the sample. A sample rack for which the dispensing operation has been completed is carried out by the carry-out mechanism 104 onto the external transfer line 101 and is transferred for subsequent treatment.

Figure 3:
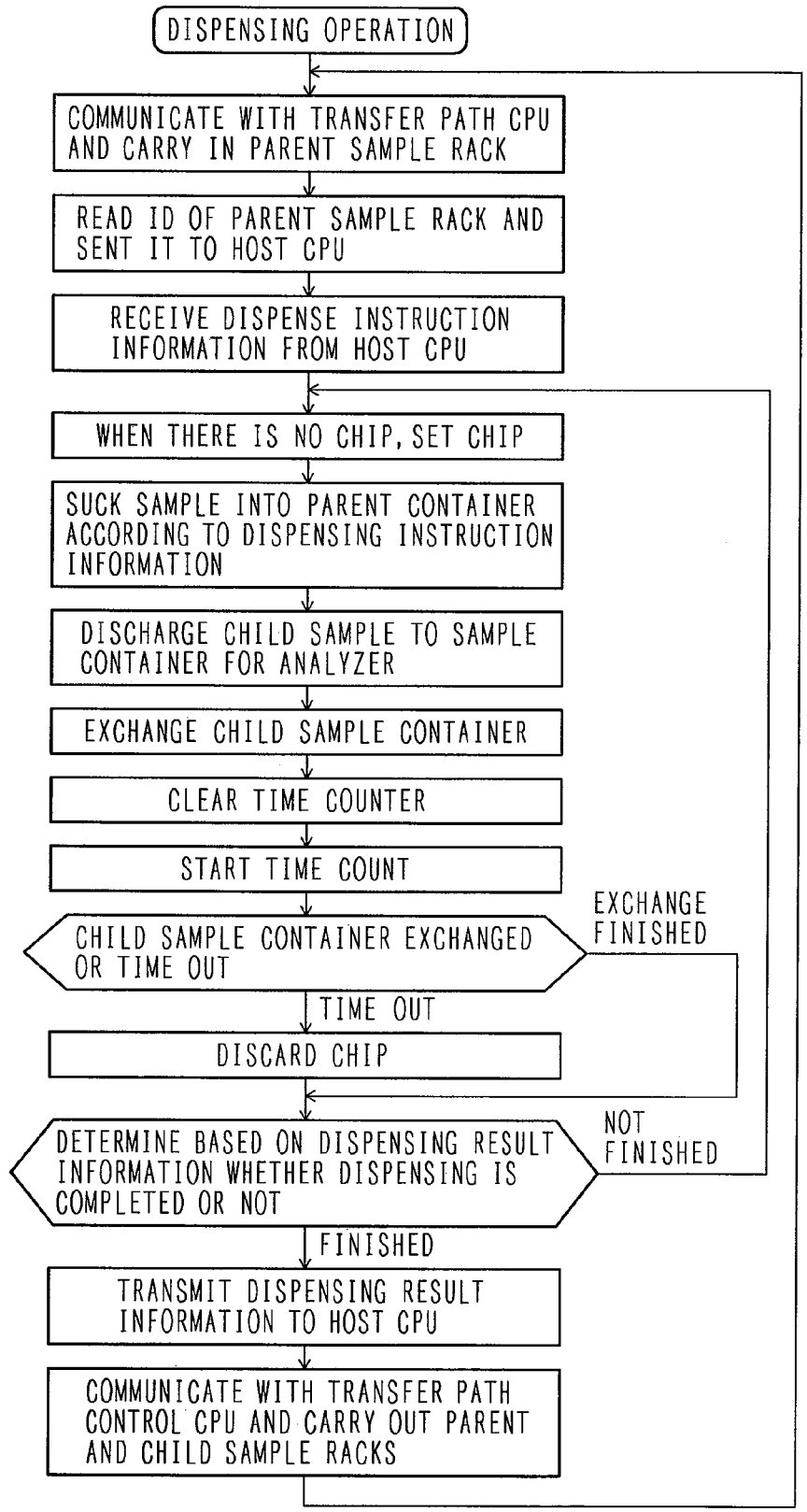
FIG. 3 is a view illustrating a nozzle chip discard flow during a dispensing step in the embodiment.

FIG. 3 is a view illustrating outline of an example of a flow of processing to be controlled by the dispensing control CPU 340.

When the parent sample racks 10a, 10b, 10c come to respective carry-in positions, the dispensing control CPU 340 communicates with the transfer path control CPU 330 to acquire instructive information for dispensing and carries the parent sample racks 10a, 10b, 10c into the dispensing device.

The dispensing control CPU 340 reads IDs of the parent sample racks 10a, 10b, 10c from the bar code or the like, and transmits the information to the host CPU, and receives instructive information for dispensing the sample.

When the nozzle chip 2 is not set on the dispensing head 1, an operation for setting the nozzle chip 2 on the dispensing head 1 is performed. The sample is sucked from the parent sample container 3 according to the instructive information for dispensing. The sample is discharged to a child sample container for an analyzer by a content instructed by the instructive information.

Then the dispensing control CPU 340 determines whether an operation of discharging the sample to all of the child sample containers has been finished, and the child sample containers are exchanged with new ones if the dispensing control CPU 340 determines that the discharging operation has been finished. The dispensing control CPU 340 measures the time it takes to exchange the child sample containers, and when exchange of all the child sample containers is not finished within a prespecified period of time, a nozzle chip 3 set on the dispensing head 1 is discarded.

A counter for time measurement may be reset at a time point of start of each dispensing operation or before measurement of time is started. After all of the child sample containers are exchanged with new ones, the dispensing control CPU 340 determines whether the dispensing operation has been completed according to the instructive information for dispensing, and when it is determined that the amount required of the sample according to the instructive information for dispensing has not yet been dispensed, the new nozzle chip 2 is set on the dispensing head 1, and then the sample is sucked into the nozzle chip 2.

When the sample is dispensed by the content instructed by the instructive information, the dispensing control CPU 340 transmits information concerning a result of dispensing to the host CPU 320. Then the dispensing control CPU 340 communicates with the transfer path control CPU 330 to transfer the parent sample racks 10a, 10b, 10c with the parent sample containers 3 set thereon respectively and the child sample racks with the child sample containers mounted thereon respectively onto transfer lines 105, 106, 107, and 108 outside the dispensing device.

To measure the time it takes for dispensing, it is required to measure any of the time it takes to exchange the child sample containers, the time when the nozzle chip is set on the dispensing head, a period of elapsed time after the end of last operation of sucking or discharging a sample, or the like. During the elapsed time, an operation of dispensing the sample cannot be performed. When the elapsed time is over a prespecified period of time, the nozzle chip is released from the dispensing head.

A configuration is preferable in which the time previously specified can be set from the host CPU or the dispensing control CPU.

Further, an operation may be carried out to discharge back the sample remaining in the nozzle chip to the original parent sample container before discard of the nozzle chip. In this case, since there is the possibility that air is also discharged, the discharge back should be started not from a tip position of the nozzle chip at the time point when the sucking operation is terminated, but from a portion above a level of a sample liquid in the parent sample container.

Then the nozzle chip is discarded. With the operations as described above, waste of a sample can be eliminated.

In the example above, description is made for a case in which exchange of child sample racks each with a number of child sample containers mounted thereon is jammed and a dispensing operation is stopped, but the present invention can also be applied to a case where a dispensing operation is stopped for each discrete child sample container.

What is claimed is:
1. A sample dispensing apparatus comprising:
   a dispensing device for dispensing a sample sucked therein;
   a dispensing head provided in the dispensing device; and
   a disposable nozzle chip detachably mounted on the dispensing head;
   wherein a sample sucked into the nozzle chip is dispensed into child sample containers while the child sample containers are replaced one by one; and
   wherein the nozzle chip is released from the dispensing head when a dispensing-suspended time elapses a prespecified period of time, the dispensing-suspended time being a period of time when a dispensing operation of the sample into the child sample container cannot be performed.
2. The sample dispensing apparatus according to claim 1, wherein a sample still remaining in the nozzle chip is returned to a parent sample container before the nozzle chip is released from the dispensing head.

3. The sample dispensing apparatus according to claim 1, wherein a new nozzle chip is set on the dispensing head before a dispensing operation is restarted.

4. The sample dispensing apparatus according to claim 1, wherein the prespecified period of time can be changed.

5. A sample dispensing apparatus comprising:
a dispensing device for dispensing a sucked sample;
a dispensing head provided in the dispensing device;
a disposable nozzle chip detachably mounted on the dispensing head; and
an XYZ mechanism provided in the dispensing device and capable of moving the dispensing head in the horizontal direction as well as in the horizontal direction,
wherein a sample is dispensed into child sample containers while the child sample containers are replaced one by one; and
wherein the nozzle chip is released from the dispensing head when a dispensing-suspended time elapses a prespecified period of time, the dispensing-suspended time being a period of time when a dispensing operation of the sample into the child sample container cannot be performed.

6. The sample dispensing apparatus according to claim 5, wherein, when the prespecified period of time elapses, the XYZ mechanism moves the dispensing head to a position where the nozzle chip is to be discarded and the nozzle chip is removed there.

7. A sample dispensing apparatus comprising:
a parent sample container in which a sample is put;
a dispensing device for dispensing a sample sucked from the parent sample container;
a dispensing head provided in the dispensing device;
a disposable nozzle chip detachably mounted on the dispensing head; and
an XYZ mechanism provided in the dispensing device and capable of moving the dispensing head in the vertical direction as well as in the horizontal direction;
wherein a sample is dispensed into child sample containers while the child sample containers are replaced one by one; and
after a dispensing-suspended time elapses a prespecified period of time, the dispensing-suspended time being a period of time when a dispensing operation of the sample into the child sample container cannot be performed, the dispensing head is moved by the XYZ mechanism to a position where the parent sample container is placed, the sample still remaining in the nozzle chip is returned to the parent sample container, and then the nozzle chip is released from the dispensing head.

* * * * *